(12) United States Patent
Stemmer (10) Patent No.: US 10,989,771 B2
(45) Date of Patent: Apr. 27, 2021

(54) METHOD FOR TRIGGERED ACQUISITION OF A MEASURED DATA SET BY A MAGNETIC RESONANCE SYSTEM, COMPUTER PROGRAM, DATA MEMORY, AND MAGNETIC RESONANCE SYSTEM

(71) Applicant: Siemens Healthcare GmbH, Erlangen (DE)

(72) Inventor: Alto Stemmer, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 20 days.

(21) Appl. No.: 16/515,386

(22) Filed: Jul. 18, 2019

(65) Prior Publication Data

US 2020/0033426 A1 Jan. 30, 2020

(30) Foreign Application Priority Data

Jul. 26, 2018 (EP) .................................. 18185777

(51) Int. Cl.
*G01R 33/28* (2006.01)
*G01R 33/36* (2006.01)
*A61B 5/055* (2006.01)

(52) U.S. Cl.
CPC ............ *G01R 33/288* (2013.01); *A61B 5/055* (2013.01); *G01R 33/36* (2013.01)

(58) Field of Classification Search
CPC ........ G01R 33/36; G01R 33/288; A61B 5/055
See application file for complete search history.

(56) References Cited

U.S. PATENT DOCUMENTS

| 8,519,706 | B2 | 8/2013 | Landschuetz | |
|---|---|---|---|---|
| 8,663,300 | B2* | 3/2014 | Camus | A61F 2/95 623/1.11 |
| 10,088,541 | B2* | 10/2018 | Paul | G01R 33/4835 |
| 10,667,760 | B2* | 6/2020 | An | A61B 5/0816 |
| 2003/0036693 | A1* | 2/2003 | Avinash | G16H 50/30 600/413 |

(Continued)

FOREIGN PATENT DOCUMENTS

DE 102009055960 A1 6/2011
DE 102012206578 A1 10/2013
(Continued)

*Primary Examiner* — Dixomara Vargas
(74) *Attorney, Agent, or Firm* — Lempia Summerfield Katz LLC (57) ABSTRACT

The disclosure relates to a method for triggered acquisition of a measured data set by a magnetic resonance system, to a corresponding computer program, to a corresponding data memory and to the corresponding magnetic resonance system. In the method, a cyclical signal is detected, which describes a cyclical change in a target object to be imaged. Cycles are automatically identified in this cyclical signal. Furthermore, at least one property of the cyclical signal is automatically determined. It is then automatically determined whether triggering of a single measurement for acquisition of some of the measured data set is permitted in an identified cycle of the cyclical signal. This determination is made as a function of the at least one determined property of the cyclical signal and a specified reference value of an acquisition parameter.

14 Claims, 3 Drawing Sheets

(56) References Cited

U.S. PATENT DOCUMENTS

| | | | |
|---|---|---|---|
| 2010/0114289 A1* | 5/2010 | Camus | A61F 2/95 |
| | | | 623/1.11 |
| 2011/0130644 A1 | 6/2011 | Stemmer | |
| 2013/0266200 A1* | 10/2013 | Miyazaki | A61B 5/055 |
| | | | 382/131 |
| 2013/0281824 A1 | 10/2013 | Stemmer | |
| 2015/0173642 A1* | 6/2015 | Blumhagen | A61B 5/055 |
| | | | 600/413 |
| 2015/0223703 A1* | 8/2015 | Abd-Elmoniem | A61B 5/7278 |
| | | | 600/413 |
| 2015/0226819 A1* | 8/2015 | Paul | G01R 33/482 |
| | | | 324/309 |
| 2016/0074674 A1* | 3/2016 | Kohli | A61B 5/0036 |
| | | | 600/484 |
| 2017/0273638 A1* | 9/2017 | An | A61B 5/0402 |
| 2017/0328975 A1 | 11/2017 | Greiser | |

FOREIGN PATENT DOCUMENTS

| | | |
|---|---|---|
| DE | 102009061198 B3 | 2/2014 |
| DE | 102016208094 A1 | 11/2017 |

\* cited by examiner

METHOD FOR TRIGGERED ACQUISITION OF A MEASURED DATA SET BY A MAGNETIC RESONANCE SYSTEM, COMPUTER PROGRAM, DATA MEMORY, AND MAGNETIC RESONANCE SYSTEM

The present patent document claims the benefit of European Patent Application No. 18185777.2, filed Jul. 26, 2018, which is also hereby incorporated by reference.

TECHNICAL FIELD

The disclosure relates to a method for triggered acquisition of a measured data set of a target object in a plurality of single measurements by a magnetic resonance system. Furthermore, the disclosure relates to a corresponding computer program or computer program product, to a data memory for a magnetic resonance system having a computer program of this kind, and to a magnetic resonance system having a data memory of this kind.

BACKGROUND

With triggered acquisition of measurement data, triggered measurement or triggered operation of a magnetic resonance system therefore, measurements are not carried out continuously, measurement data recorded or acquired therefore, and instead only once certain conditions (e.g., trigger conditions) are met or a particular event (e.g., trigger event) has occurred in each case. Measuring, a respective acquisition of measurement data therefore, is then triggered, activated, or induced. An application of this is, for example, to synchronize the acquisition of measurement data with the breathing of a patient.

SUMMARY AND DESCRIPTION

The scope of the present disclosure is defined solely by the appended claims and is not affected to any degree by the statements within this summary. The present embodiments may obviate one or more of the drawbacks or limitations in the related art.

The object of the present disclosure is to enable improved image quality with simultaneously particularly straightforward usability for triggered data acquisition.

The method disclosed herein is used for triggered acquisition of a measured data set of a target object in a plurality of single measurements by a magnetic resonance system, for example, by a magnetic resonance tomograph (MRT) therefore. Within the meaning of the present disclosure, a single measurement should not necessarily be taken to mean acquisition or detection of a single data point or measured value. Instead, a single measurement within this meaning is a portion of the acquisition of the entire measured data set that is not interrupted over time. Therefore, during a single measurement, a plurality of measured values may be detected, recorded, or acquired, for example, a complete slice of the target object. A period may then elapse between two single measurements during which no data is acquired for the measured data set.

The target object may be a patient or a particular area of tissue without being limited hereto within the scope of the present disclosure.

In the method, a cyclical signal is detected, which describes a cyclical change in the target object or part of the target object. The cyclical change may be a repetitive movement of the target object or part of the target object. The cyclical signal or the cyclical change may be detected by the magnetic resonance system itself, for example, by an MR navigator sequence or by a detection device specifically provided for this purpose. The detection device may include a pneumatic sensor, a chest strap, an electromagnetic sensor, and/or the like. Furthermore, in the method, automatic cycles of the cyclical signal continue to be identified during subsequent acts of the method as well. For this, the detected cyclical signal may be automatically processed, analyzed, or evaluated with a corresponding data processing device.

In a further method act, at least one property of the cyclical signal is then automatically determined. This property may be a cycle duration, a period duration, a frequency, or a current value of the cyclical signal, in particular, in relation to a specified reference value. This will be explained in more detail below in conjunction with developments and embodiments of the method.

In a further method act, it is automatically determined whether, in a particular identified cycle of the cyclical signal, triggering of one of the single measurements is permitted, as a function of the at least one determined property of the cyclical signal and a specified reference value of an acquisition parameter. This acquisition parameter may be specified for the acquisition of the measured data set. The reference value may serve, for example, as a comparative value or as a basis for calculation, does not necessarily have to be a parameter or parameter value used directly during one of the single measurements by the magnetic resonance system for the actual acquisition of measurement data therefore, the actual measurements therefore. As will be explained in more detail below, the reference value may be a reference repetition time or protocol repetition time, although a repetition time different from this may then ultimately be used for the acquisition of the measured data set. The repetition time used may then have, for example, a particular relationship to the reference repetition time, for example, be at least just as long.

For example, a particular pattern or a particular rule may therefore be determined or defined, according to which it may be determined for every cycle, in particular, also future cycles, of the cyclical signal whether triggering of one of the single measurements in each case is permitted in the respective cycle. Similarly, it may be individually detected or measured, defined for each identified cycle, for example, during the runtime, during the respective cycle of the cyclical signal therefore, whether one of the single measurements may or may be triggered in this respective cycle.

That the triggering of one of the single measurements is permitted is a necessary condition for the fact that one of the single measurements is actually being carried out in the respective cycle, corresponding magnetic resonance data (MR data, MR measurement data) is being acquired or recorded for the measured data set therefore. In particular, some or a plurality of further conditions or events may be specified in order to actually trigger, activate therefore, one of the single measurements in a cycle in which triggering of one of the single measurements is permitted. If triggering of one of the single measurements is not permitted in a particular cycle, then irrespective of whether these further conditions or events are met or have occurred, none of the single measurements is carried out, the respective cycle is omitted therefore.

As already indicated, the acquisition parameter may be a reference duration, which indicates a minimum time frame, which in each case lies between two successive single measurements or associated triggering or trigger events. This reference time may therefore be the protocol repetition time already mentioned, which is defined by a protocol. A protocol of this kind may be selected, for example, for the acquisition of the measured data set or as an initial setting for this, and optionally be adjusted. Similarly, the acquisition parameter may be at least one maximum Specific Absorption Rate (SAR) value, which in at least one time interval of a particular specified length during acquisition of the measured data set or during an overall measurement or examination of the target object may not be exceeded respectively. This will likewise be explained in more detail below in conjunction with corresponding embodiments and developments of the method.

In previous, known triggered measuring methods, delayed activations, (what are known as mistriggers), may occur, in particular, if the reference time is a reference repetition time for the measurement and is of a similar length or size as a cyclical length or cyclical duration of the cyclical signal. By contrast, the present disclosure enables a triggered measurement or data acquisition, which is robust with respect to such scenarios. If, for example, no single measurement is permitted in a particular cycle, then no single measurement is made during this cycle either when all other necessary conditions or triggers are met or provided, and instead the next single measurement may be made at the earliest only in the next cycle again, in particular, after it or its beginning has been clearly identified. Consequently, delayed activations of single measurements are avoided. Delayed activation of a single measurement may occur in the previously known triggered measuring methods for example if the remaining necessary trigger conditions are met before the reference time since the last trigger, the last single measurement therefore, has elapsed.

The present disclosure may advantageously prevent the situation where the single measurements are started at delayed, non-optimum therefore, instants or phases of the cyclical signal. The present disclosure may therefore advantageously and reliably provide that the single measurements are started at an optimum instant. This optimum instant may be specified or be determined by the remaining necessary conditions in a specified manner. Overall, the present disclosure therefore achieves or enables improved consistency of the measurement data of the measured data set and therewith ultimately improved data or image quality. Owing to the robustness achieved by the present disclosure, advantageously, for example, the reference repetition time of a specified measuring sequence may be selected or specified to be greater than previously. In particular, this reference repetition time of pre-produced acquisition parameter sets, protocols therefore, may be equal to or only slightly shorter than a typical breathing frequency or breathing period of a typical patient without adversely affecting the image quality hereby. In addition, an ultimately unnecessary limiting of other sequence or protocol parameters may therefore be prevented.

The measured data set may be acquired by carrying out the single measurements. For example, one or more magnetic resonance image(s) may be calculated, (e.g., reconstructed), from the measured data set. The one or more magnetic resonance images may be displayed for example to a user, for example, on a screen.

In previous triggered measuring methods, by contrast, the reference time or reference repetition time may be selected to be a good deal shorter than, for example, the typical breathing periods in order to avoid mistriggers, although this may lead, on the basis of this unnecessarily short reference repetition time, to the automatic determination that sequence or protocol parameters, (such as a flip angle or a number of slices of the target object to be imaged), have to be reduced, and this ultimately likewise leads to a deterioration in image quality and/or reduced efficiency of the measurement.

In addition, the present disclosure improves robustness with respect to user errors or a lack of understanding on the part of the respective user. If, for example, during the course of a SAR simulation or SAR projection, it is found that it is anticipated that a maximum SAR value will be exceeded during a planned measurement, then a proposal may be put to a user to lengthen the reference repetition time for the measurement. If the user follows this proposal and lengthens the reference repetition time, for example, to beyond the length of the cycle, a mean period duration of the cyclical signal therefore, then in conventional methods this may lead to the delays or mistriggers. It cannot generally be assumed in this connection that a correlation between the reference repetition time, mistriggers caused thereby and a resulting image quality is necessarily known to the respective user. A best-possible image quality is reliably provided by the present disclosure even in scenarios such as these.

In an advantageous embodiment, a cycle point, which the cyclical signal has to have reached in one cycle respectively, is defined as the necessary condition for triggering the single measurements. In each cycle the cycle point may therefore represent or indicate a trigger instant for activation of one of the single measurements. This may advantageously therefore provide that each of the single measurements are activated or started at mutually corresponding points, cycle points or phases therefore, of the cyclical signal. For example, a particular value of the cyclical signal may be specified as the cycle point, which value the cyclical signal has to have reached or exceeded from a specified direction, for example, increasing from below therefore, in order to trigger one of the single measurements. This is a necessary condition, however, and not a solely sufficient condition for triggering one of the single measurements because this triggering firstly is permitted in the respective cycle. Depending on application, the cycle point may also be a turning point or a reversal point, for example, a local extreme value of the cyclical signal. Similarly, the cycle point may be a specified time interval or be determined by a specified time interval, which has elapsed or has to have elapsed since such a turning or reversal point or extreme value of the cyclical signal.

Similarly, a second cycle point may be specified, which the cyclical signal, as a necessary condition for triggering one of the single measurements, has not reached or exceeded in the respective cycle yet. This may be an end value, a reversal point or a typical, average, or expected maximum value. A region or window, a section of each cycle of the cyclical signal therefore, may thus be defined by these two cycle points, in which section the cyclical signal or a value of the cyclical signal is located in each case as a necessary condition for triggering one of the single measurements.

In a further advantageous embodiment, a mean duration $L_m$, a mean length of time therefore, of the identified cycles of the cyclical signal is determined as the at least one property of the cyclical signal. The mean duration $L_m$ is therefore a mean cycle duration or period duration of the cyclical signal. A reference repetition time or reference duration $TR_{prot}$ is then specified as the reference value or as the acquisition parameter. Furthermore, the smallest whole positive number $n \geq 1$ is then determined, so an n-multiple of the determined mean duration $L_m$ is longer than the specified reference repetition time $TR_{prot}$. Triggering of the single measurements is then permitted only in each $n^{th}$ cycle of the cyclical signal. If the specified repetition time $TR_{prot}$ is short compared to the mean duration $L_m$, then n is determined as 1 and one of the single measurements may be triggered in each cycle, during each period therefore, of the cyclical signal.

Otherwise, if, for example, the specified reference time or reference repetition time $TR_{prot}$ is of a similar length or is longer than the mean duration $L_m$, n may be determined as >1. One of the single measurements may then be triggered only in each $n^{th}$ cycle, (for example, in every second or third or fourth cycle of the cyclical signal), even if the remaining necessary conditions for activating one of the single measurements are met at least once in each case in each cycle of the cyclical signal. Therefore, one or more cycle(s) may be omitted, (e.g., pass), during which none of the single measurements is activated between cycles in which one of the single measurements is activated or carried out.

This may result in a time required overall for acquisition of the complete measured data set being lengthened, but it is provided that each of the single measurements may be carried out at an optimum instant or during an optimum phase of the cyclical signal. In addition, it is provided that a resulting, effective, (e.g., actual), repetition time $TR_{eff}$ is constant and uniform during acquisition of the measured data set, irrespective of unavoidable, (e.g., physiologically induced), variations in the duration of the cycles of the cyclical signal. If the cyclical signal is, for example, a respiration curve of a patient, then the duration of the cycles, (e.g., the cycle duration or period length), is subject to an unavoidable natural variation. It is possible to provide that there is the same number of breathing cycles between each of the single measurements and that each single measurement is carried out, for example, in a respectively particularly suitable, such as a particular, specified, phase, (e.g., at the end of an exhalation), and not with a delay, for instance owing to an unfavorable interaction between the specified reference repetition time $TR_{prot}$ and the cycle length.

The latter may be the case, for example, if, with a conventional triggered method, the reference repetition time specified there is a fraction longer than the mean length of the breathing cycle and this deviation then adds up over several cycles, so that—owing to the variance in the cycle lengths, irregular—intervals one breathing cycle is omitted or, for example, owing to an inertia during identification of a respective phase of the cycle, a single measurement is started late, for example, at the beginning of the next breathing cycle, when the patient is already inhaling again therefore.

For determining the mean duration $L_m$, a learning phase may be provided during which, over a plurality of cycles, only the cyclical signal is detected but no measurement data is recorded for the measured data set. The mean duration $L_m$ may then be determined once based on the cycles detected during this learning phase. Subsequently, during the subsequently continued detection of the cyclical signal and during the single measurements therefore, during the acquisition of the measurement data for the measured data set therefore, the cycles of the cyclical signal may then be automatically counted or numbered in each case in order to permit or prevent triggering of one of the single measurements according to the determined value of n. Temporally uniform triggering of the single measurements enabled as a whole in this way ultimately results in improved data or image quality of the measured data set.

In an advantageous development, the empirical standard deviation σ of the durations of the identified cycles of the cyclical signal is determined. The number n is then determined such that the condition in equation (1) is met:

$$(n \cdot L_m - x \cdot \sigma) > TR_{prot} \quad (1)$$

where x is a free parameter with a specified value. The free parameter x may have whole or non-whole values. A sensitivity of the method may be set by way of the free parameter x. A value of the free parameter x may therefore be set or specified by a respective user according to need or application. In an embodiment, the value of the free parameter x is specified from the interval 0.5 to 2, or from the interval 0.5 to 1. These intervals may be closed. It has been found that particularly good results may be achieved if the value of x lies in these intervals. By taking into account the standard deviation σ, the robustness of the method may be further improved and it may therefore be particularly reliably provided that the single measurements are actually carried out at a uniform interval, regularly every n cycles therefore. Compared to a corresponding use of a specified fixed value, use of the standard deviation has the advantage of taking into account individual properties of the respective target object. Whether a respective patient has a relatively regular or irregular breathing frequency may therefore be considered, for example. As a result, improved robustness with a simultaneously minimum time overall for acquisition of the measured data set may be achieved.

In a further advantageous development, the identified cycles of the cyclical signal are consecutively numbered with a consecutive cycle number k. One of the cycle numbers k is then allocated to each acquired measured value s of the cyclical signal. In other words, for each acquired measured value s, it is therefore determined in which cycle the respective measured value was acquired. The allocation may be made in the form of an index, so a measured value $s_k$ has been acquired in the cycle k therefore. For each of the detected, numbered cycles a maximum value of the cyclical signal in this cycle is then determined and from this a sequence of these maximum values is generated. The maximum value may be a largest value or an end value, a value acquired last in the respective cycle therefore. For this, each of the measured values s may be acquired as a tuple from a signal value and a time stamp. As a duration of a cycle k, a time interval between the maximum value of the cycle k and the maximum value of the immediately preceding cycle k−1 may in each case then be defined or calculated. The duration of a cycle may then match the time interval between two successive maximum values therefore. The variables $L_m$ and σ of the condition (1) may then be determined from the sequence of maximum values therefore. Use of the maximum values may enable this particularly easily, accurately and reliably. In addition, uniform triggering of the single measurements in every $n^{th}$ cycle may thus be enabled particularly easily, reliably and consistently. The maximum values may also define a respective start or a respective end of the cycles.

The mean duration $L_m$ of the identified cycles may be determined as a mean, (e.g., as an arithmetic mean), or as a median. For example, at every signal point or measured value s of the cyclical signal, a signal value and an associated time stamp are acquired and a breathing interval or cycle k allocated thereto, and in addition to each concluded breathing interval or cycle k, a maximum value $s_{max}$ determined.

If the cyclical signal is a respiration curve, then the maximum value of the cycle k may match a state of maximum inhalation during this cycle k. This is particularly advantageous because an inhalation peak in the cyclical signal indicating this maximum inhalation may be more acute or steeper than a corresponding signal form in the case of a maximum exhalation, (an exhalation peak therefore), so the respective duration of the cycles, (breathing intervals therefore), may be advantageously determined particularly accurately and consistently. A sequence of tuples $(s_k, t_k)$ therefore results, including a signal value $s_k$ and an associated time stamp $t_k$, for the maximum of the cycles k. If, for example, during the learning phase, a total of K breathing intervals is counted, then the mean duration $L_m$ may be determined as an arithmetic mean over K−1 compete breathing intervals and the associated empirical standard deviation σ may be determined as:

$$L_m = \overline{dt} = \frac{1}{K-1} \sum_{k=2}^{K} (t_k - t_{k-1}) \quad (2)$$

$$\sigma = \sqrt{\frac{1}{K-1} \sum_{k=2}^{K} ((t_k - t_{k-1}) - \overline{dt})} \quad (3)$$

If, instead, the mean duration $L_m$ should be determined as a median, then the K−1 durations are ordered in an increasing sequence as represented in equation (4):

$$dt_k = (t_k - t_{k-1}), k = 2, \ldots, K \quad (4)$$

where a new sequence $\widetilde{dt_k}$ is produced where $\widetilde{dt_i} \leq \widetilde{dt_j}$ for i<j. Then:

$$dt_{median} = \begin{cases} \widetilde{dt}_{\frac{K}{2}+1}, & \text{for } K \text{ even} \\ \frac{1}{2} \left( \widetilde{dt}_{\frac{K+1}{2}+1} + \widetilde{dt}_{\frac{K+1}{2}} \right), & \text{for } K \text{ odd} \end{cases} \quad (5)$$

and $$\tilde{\sigma} = \sqrt{\frac{1}{K-1} \sum_{k=2}^{K} (dt_k - dt_{median})} \quad (6)$$

In a further advantageous embodiment, as the at least one property, it is determined at which instant $t_n$ in the respective determined cycle an acquired measured value of the cyclical signal exceeds a specified threshold value or lies in a particular value interval for the first time. This particular value interval may also be called an acquisition window. The particular value interval may be specified or automatically defined, for example, based on measured values of the cyclical signal acquired during the learning phase, for example, in respect of an amplitude of the cyclical signal or the like. The reference repetition time $TR_{prot}$ is specified as the reference value or the acquisition parameter. Triggering is then permitted in the respective determined cycle only when at least the reference repetition time $TR_{prot}$ has elapsed between the preceding single measurement and the instant $t_n$ in each case. In one respective cycle, a single measurement may only be activated therefore if at least the reference repetition time $TR_{prot}$ has elapsed since the preceding single measurement respectively before the first measured value, which exceeds the specified threshold value or falls in the acquisition window, is acquired in the respective cycle. If a measured value, which exceeds the specified threshold value or falls in the acquisition window, has already been acquired in the respective determined cycle, however, before the reference repetition time $TR_{prot}$ has elapsed since the last single measurement respectively, (in particular, since the beginning or activation thereof), then a single measurement is not triggered in the respective cycle.

That the current value or measured value of the cyclical signal has to lie in the determined value intervals may therefore be understood or used as a necessary but not solely sufficient trigger condition, condition for triggering therefore.

If, therefore, the value of the cyclical signal point acquired at instant $t_n$ is the first measured value of the cyclical signal, which falls in the acquisition window during the current cycle respectively, then triggering in the respective determined cycle is permitted only when at least the reference repetition time $TR_{prot}$ has elapsed between the preceding single measurement and the instant $t_n$ respectively. In other words, a single measurement is only carried out during a determined cycle when at the instant at which the signal value of a measured value acquired during this cycle falls in the acquisition window for the first time, at least the reference time $TR_{prot}$ has elapsed since the last single measurement.

A cycle of the cyclical signal may include a falling and a rising edge of the cyclical signal respectively. If the cyclical signal then passes, for example, during the rising edge, the determined value interval in a cycle before the specified repetition time $TR_{prot}$ has expired or elapsed since the last single measurement, then triggering of one of the single measurements is not permitted for this cycle. The situation may thereby be prevented where after expiry of the specified reference repetition time $TR_{prot}$, a single measurement is triggered with a delay, if, for example, the cyclical signal occurs again in the falling edge in the determined value interval. Effectively, triggering of one of the single measurements in a determined cycle is therefore not permitted precisely when adherence to the specified reference repetition time $TR_{prot}$ in a conventional triggered measuring method would lead to delayed triggering, a mistrigger therefore. Overall, there is therefore continued assurance that the single measurements are triggered consistently at an optimum instant or an optimum phase during the course of the cyclical signal, while, at the same time, a time required overall for acquisition of the measured data set is minimized.

In a further advantageous embodiment, as the at least one property, it is determined at which instant $t_n$ in the respective determined cycle an acquired value of the cyclical signal exceeds a specified threshold value or lies in a particular value interval for the first time. Reference is made in this regard to the above statements. However, a maximum SAR value $SAR_{max}$ for at least one specified time interval, which includes the instant $t_n$, is specified as the reference value or the acquisition parameter here. This value $SAR_{max}$ may be individually precalculated or adjusted for the respective target object, (e.g., the respective patient), to limit stress on the patient as required. Triggering is permitted in the respective determined cycle only if the specified maximum SAR value $SAR_{max}$ would not be exceeded by one of the single measurements triggered at instant $t_n$.

The specified maximum SAR value may include a plurality of SAR single values, which may be specified for a plurality of specified time intervals of different length, different categories of time intervals therefore. For example, a first SAR single value may be specified therefore for time intervals of 2 s duration, a second SAR single value for time intervals of 10 s duration, and a third SAR single value for time intervals of 60 s duration. The SAR single values may have different magnitudes as a function of a length or duration of the time interval for which they are specified. Time intervals of a particular category, durations therefore, may continuously repeat themselves in each case. This means that a total time of an examination or measurement of the target object may be divided completely into time intervals of each category and the respective SAR single value or the maximum SAR value$_{max}$ may not be exceeded in any of these time intervals. A particular instant may therefore simultaneously be included in a plurality of time intervals of different categories or durations.

Triggering is therefore permitted in the respective particular cycle only when at the instant at which the signal value of a measured value acquired during this cycle falls in the acquisition window for the first time, the next one of the single measurements respectively does not exceed any of the SAR values in the respective time intervals.

A respectively current SAR value, (e.g., achieved or already applied during the previous single measurements), over the previous acquisition of data for the measured data set therefore or the previous examination of the target object may be continuously simultaneously recorded or simulated. If the target object or, for example, another part of the respective patient has already been imaged even before the beginning of the acquisition of the current measured data set by the magnetic resonance system, then accumulated SAR values, energy inputs therefore, may also be considered in the process.

Similarly, a contribution of each or the next single measurement respectively may then be simulated or estimated in order to (e.g., automatically) determine whether SAR$_{max}$ or one of the corresponding single values would be exceeded in one of the time intervals by the respective single measurement if it were to be activated at the current instant $t_n$ respectively. This may be carried out up to the instant $t_n$ respectively therefore. Similarly, it is possible to begin a corresponding calculation at the instant $t_n$ in order to decide about whether one of the single measurements is triggered in the current cycle. Time intervals running in each case at the instant $t_n$ and/or during the planned next single measurement may be considered in the process.

In other words, a single measurement is therefore carried out during a particular cycle only when at the instant at which the signal value of a measured value acquired during this cycle falls in the acquisition window for the first time and none of the SAR values is exceeded during the respective time intervals by the next single measurement respectively.

In other words, a cycle is omitted therefore, none of the single measurements is activated in this cycle therefore, if SAR$_{max}$ or one of the single values would be exceeded by this single measurement. In particular, the respective cycle is then completely omitted, the next single measurement only permitted again therefore once the beginning of a new cycle of the cyclical signal has been clearly identified.

The case may occur where in the described manner the cyclical signal falls in the particular value interval at the beginning of the next cycle or during the corresponding rising and falling edge. Furthermore, one of the SAR values in at least one of the then current time intervals may be exceeded by the respective next single measurement, for example, during the rising edge, but not during the subsequent falling edge. In a conventional method the single measurement would then be triggered with a delay during the falling edge. The cyclical signal is then not in an optimum phase, however, so the conventional triggered measuring methods would in this case lead to a mistrigger and therefore ultimately to a deterioration in image quality, while it is precisely this that is prevented by the present method. In this embodiment, optimum data or image quality requiring a minimum total measuring time for acquisition of the measured data set may therefore advantageously be achieved.

In a further advantageous embodiment, the single measurements are each shorter than one cycle, than one cycle length or period duration therefore, of the cyclical signal. In other words, measurement data for the measured data set is therefore only acquired during particular parts or during a particular phase of the cyclical signal, for example, according to or by an MR measuring sequence that is only active then. Advantageously, the improved image quality may be particularly reliably and consistently achieved hereby. Similarly, it is advantageously possible to use the same magnetic resonance system for both detecting the cyclical signal and for acquisition of the measurement data for the measured data set even if the magnetic resonance system cannot achieve this simultaneously. The cyclical signal may then be detected only at the times or in the phases of the cyclical signal at/in which no measurement data is acquired for the measured data set. However, this may be sufficient for identifying and characterizing the cyclical signal, for example, for determining a current phase of the cyclical signal therefore. The measurement data may be acquired for the measured data set only during the exhalation phase for a specified period. The specified duration or time for each of the single measurements may be specified as a function of the determined mean duration of a cycle of the cyclical signal, the mean cycle duration therefore, in such a way that the single measurement is concluded in a cycle of typical, (e.g., mean), length at or even before the end of the exhalation phase. In this way the knowledge that measurement data acquired during this phase of the breathing cycle may lead to particularly good image quality may be advantageously utilized.

In a further advantageous embodiment, a heartbeat is detected as the cyclical signal.

In a further advantageous embodiment, a respiration curve is detected as the cyclical signal. The respiration curve describes a movement of the target object, here a patient or part of the patient therefore, caused by breathing, inhalation and exhalation therefore. In order to detect the respiration curve, for example a movement, a cyclical or rhythmic expansion therefore, of the chest of the patient or for example a corresponding movement of a diaphragm of the patient may be detected. Detection of the respiration curve as the cyclical signal is particularly advantageous here because breathing may be accompanied by significant movements of the patient and consideration of the respiration curve and at least one particular property during acquisition of the measured data set may accordingly lead or contribute to a significant improvement in the image quality.

In an advantageous development, different phases or breathing phases of the respiration curve, (e.g., the "inhalation" phase and the "exhalation" phase), are automatically identified and triggering of one of the single measurements permitted only during the "exhalation" phase. For this, the current breathing phase in each case may be allocated to each acquired value or measured value of the cyclical signal. A necessary condition for triggering one of the single measurements may therefore be that the "exhalation" breathing phase has been allocated to a value acquired last in each case. During the initial learning phase, during which the cyclical signal is detected for the first time and no measurement data has yet been acquired for the measured data set, the "unknown" breathing phase may likewise be allocated to a measured value or signal point of the cyclical signal, for example, if there are not yet enough measured values available in order to clearly determine the current phase in each case. Once the "inhalation" phase or "exhalation" phase has been allocated to a measured value of the cyclical signal, however, then thereafter these two phases are only switched between and the "unknown" phase is not allocated again.

An absolute or a relative threshold value, (for example, a minimum spacing from a minimum value of the cyclical signal), may be specified, moreover, which the cyclical signal has reached or exceeded during the "exhalation" phase above as a necessary condition for triggering one of the single measurements. As a result, the single measurements cannot be triggered immediately after the beginning of the "exhalation" phase, so the measurement data may be acquired for the measured data set particularly reliably and consistently and particularly good image quality may be achieved accordingly. Similarly, a further threshold value may be specified in which the cyclical signal is currently a necessary condition for triggering one of the single measurements. This may therefore correspond to the determined value interval already mentioned in the present case at a different location.

To automatically recognize or determine the different phases of the respiration curve, a corresponding data processing algorithm may be used, for example, based on calculation of a gradient of the cyclical signal, a comparison of a current measured value respectively with preceding measured values or an image recognition.

A further aspect, a computer program or computer program product is disclosed, which encodes or represents the method acts of at least one embodiment of the method and is adapted for loading in a data memory of a magnetic resonance system in order to carry out the method acts. The computer program may include program code to carry out the method when the computer program is executed by the magnetic resonance system, in particular, a corresponding data processing device of the magnetic resonance system.

A further aspect of the disclosure is a, (e.g., electronic and/or electronically readable), data memory or data carrier in which a program code is stored, which includes at least one embodiment of the computer program. Therefore, the data memory may be the data memory mentioned in conjunction with the computer program. The program code stored in the data memory may be designed and configured to be automatically executed by a processor device (which may be part of the magnetic resonance system) to carry out the method, to induce the implementation or execution of the method therefore. The processor device may be or include a microprocessor or microcontroller. Further control instructions for the data processing device, processor device, and/or magnetic resonance system may be stored or encoded in the data memory, moreover, in particular, as part of the stored program code.

A further aspect of the disclosure is a magnetic resonance system for triggered acquisition of a measured data set of a target object, (e.g., a patient or part of a patient), in a plurality of single measurements. For this, the magnetic resonance system includes a detection device for detecting a cyclical signal, which describes a cyclical change in the target object. The magnetic resonance system further includes a measuring device for acquisition of the measured data set, and a data processing device. This data processing device includes a data memory and a processor device connected thereto for executing the program code stored in the data memory. In other words, the magnetic resonance system is therefore configured to carry out the method. Accordingly, the magnetic resonance system may be the magnetic resonance system mentioned in conjunction with the remaining aspects of the present disclosure, in conjunction with the method, the computer program, and/or the data memory therefore. The magnetic resonance system may accordingly have some or all the properties and/or elements or components mentioned in conjunction with the remaining aspects of the present disclosure.

In the same way, measures or procedures, which are mentioned or described in conjunction with the computer program, the data memory, and/or the magnetic resonance system, may be part of the method or supplement or develop it.

The properties and developments of the method, of the computer program, of the data memory, and of the magnetic resonance system disclosed previously and hereinafter as well as the corresponding advantages may analogously each be reciprocally transferred between these aspects of the disclosure. The disclosure therefore also includes those developments of the method, the computer program, the data memory and the magnetic resonance system, which have embodiments which, in order to avoid unnecessary redundancy, are not explicitly separately described here in the respective combination or for each of these aspects of the disclosure.

BRIEF DESCRIPTION OF THE DRAWINGS

Further features, details and advantages of the present disclosure result from the following description of exemplary embodiments and with reference to the drawings, in which.

DETAILED DESCRIPTION

In the exemplary embodiments herein, the described components of the embodiments are each individual features of the disclosure which should be considered independently of each other and which each also develop the disclosure independently of one another and should therefore also be regarded, individually or in a combination other than that shown, as part of the disclosure. Furthermore, the described embodiments may also be supplemented by further features of the disclosure already described.

In the case of measurements, when imaging a patient by a magnetic resonance system, radio frequency or RF pulses played out as part of a corresponding MR sequence may lead to undesirable heating of the patient due to electromagnetic energy introduced into the patient in the process. This heating is measured or quantified with the aid of the Specific Absorption Rate (SAR), which indicates the electromagnetic energy (e.g., RF energy), which is absorbed in a particular time interval per kilogram of body weight. A maximum permissible value for the SAR is legally limited and may be checked or estimated by the magnetic resonance system during the runtime. If a correspondingly specified limit value is reached or exceeded during the runtime, during a measurement or examination therefore, then the corresponding measurement is stopped. Following such a stop, as a rule, no or only an incomplete image calculation is possible.

To avoid such measuring stoppages therefore, before the measurement, a SAR value that will presumably be achieved during the measurement, by the MR sequence or pulse sequence used in each case therefore, is simulated or at least approximately calculated before the measurement. If the result of this is that the limit value will or would presumably be exceeded, then different parameters of the MR sequence or a protocol are adjusted for the measurement. To reduce the SAR value, for example, an excitation or flip angle of an RF pulse of the MR sequence may be reduced or a repetition time TR, the time which elapses between two successive RF pulses for excitation of a particular slice of the patient therefore, may be lengthened.

A triggered measurement in magnetic resonance imaging or magnetic resonance spectroscopy is a method in which in each case part of the MR sequence, for example, in each case an RF pulse for excitation therefore, is activated by a trigger, for example, when a particular specified condition is met and/or a particular specified event has occurred therefore. A trigger of this kind may be specified and monitored, for example, based on breathing, and this may then be referred to as respiration triggering. Compared to a continuous, non-triggered measurement, movement artifacts, which may occur owing to a breathing movement during breathing, may be reduced by the respiration triggering in that the measurement is synchronized with the breathing of the patient. The breathing of the patient is detected for this purpose.

MR measurement data, from which ultimately an image may be reconstructed, is recorded or acquired, for example, in what are known as acquisition phases (also "imaging phase"). These acquisition phases may each be shorter than a breathing cycle and in the present case are each started in a particular breathing phase of the patient, at a particular instant or in a particular phase or time frame of the breathing cycle therefore, which is the same for all acquisition phases.

For example, a particular slice of the patient is excited once per breathing cycle, with one breathing cycle including one complete inhalation and one complete exhalation. The resulting actual repetition time of the measurement or the MR sequence used is then determined by the breathing or a breathing frequency of the patient. The constant repetition time specified in a non-triggered sequence or measurement is replaced in a triggered measurement, for example, for calculation purposes or for illustration by what is known as an effective repetition time $TR_{eff}$, which in the present example is equal to a mean length of a breathing cycle of the patient. With a respiration-triggered measurement or sequence of this kind the resulting actual SAR value depends on the breathing of the patient therefore. This is individual to the patient and may be irregular, so an accurate prediction of the SAR value that results during the measurement is not possible.

To avoid measuring stoppages during a respiration-triggered MR measurement, a pre-calculation of the SAR value presumably achieved during the MR measurement and optionally a corresponding adjustment of parameters of the MR sequence or a corresponding protocol may occur on the basis of what is known as a protocol TR value, a specified reference time or protocol or reference repetition time $TR_{prot}$ therefore. This protocol or reference repetition time $TR_{prot}$ may be specified as part of the sequence or the protocol or be specified by a user and be guided for example by empirical values. $TR_{prot}$ may be specified for example as 2.4 s. An actual length of a breathing cycle of an individual patient may be significantly longer by contrast, (e.g., it may be 3 to 6 seconds). During the runtime, during the MR measurement therefore, the reference repetition time $TR_{prot}$ determines a minimum time between two successive triggers. A trigger is therefore only generated, (e.g., a single measurement or an RF pulse for excitation is only activated), if a time that has elapsed since the last trigger or trigger event is at least as long as the specified reference repetition time $TR_{prot}$. The actual SAR value, which is then produced during the MR measurement, is consequently less than or equal to the SAR value pre-calculated on the basis of the specified reference repetition time $TR_{prot}$, which optionally already adheres to the legal requirements for the maximum SAR value $SAR_{max}$ by way of a corresponding adjustment of parameters of the MR sequence.

If the specified reference repetition time $TR_{prot}$ is chosen to be shorter than a minimum length of a breathing cycle of the patient, as a rule, this mechanism does not affect the respiration triggering. If a desired breathing phase, which is specified as the trigger, is identified, then owing to the reference repetition time $TR_{prot}$ that is chosen to be short compared to the length of the breathing cycle, the time elapsed since the last trigger is longer than the specified reference repetition time $TR_{prot}$ and the corresponding single measurement or the corresponding RF pulse for excitation may be activated or generated.

One problem in this connection may be, however, that the SAR value predicted or pre-calculated based on the specified reference repetition time $TR_{prot}$ may be significantly higher than the actual SAR value resulting during the MR measurement. The specified reference repetition time $TR_{prot}$ is therefore chosen to be short in order to not affect or disrupt the respiration triggering, but the actual SAR value is unknown owing to the breathing frequency of the patient that is not known in advance. For safety reasons, (e.g., in order to adhere to the legal requirements for the maximum SAR value $SAR_{max}$), the parameters of the MR measurement or sequence are therefore adjusted or set using the SAR value pre-calculated based on the specified reference repetition time $TR_{prot}$. This may have an adverse effect on resulting data or image quality and/or an efficiency of the MR measurement, however. The latter is, for example, the case when a number of slices, from which MR measurement data is acquired in one breathing cycle, is reduced in order to adhere to the maximum SAR value $SAR_{max}$. Because the pre-calculated SAR value may be much higher than the actual SAR value, (e.g., with a relatively long breathing interval or breathing cycle), this kind of adjustment of the parameters for the MR measurement or sequence in respect of adherence to the specified maximum SAR value $SAR_{max}$ may ultimately be unnecessary or a lower reduction may have been sufficient.

If, on the other hand, the specified reference repetition time $TR_{prot}$ is chosen such that it is at least as long as a mean breathing cycle of the respective patient, then the SAR value pre-calculated based on the specified reference repetition time $TR_{prot}$ is, as a rule, only slightly smaller than the actual SAR value, matches this better therefore. An unnecessary limitation of the parameters of the MR measurement or sequence is avoided hereby. With conventional respiration-triggered measurements adverse, in other words undesirable, influencing of the respiration triggering may then occur, however.

Figure 1:
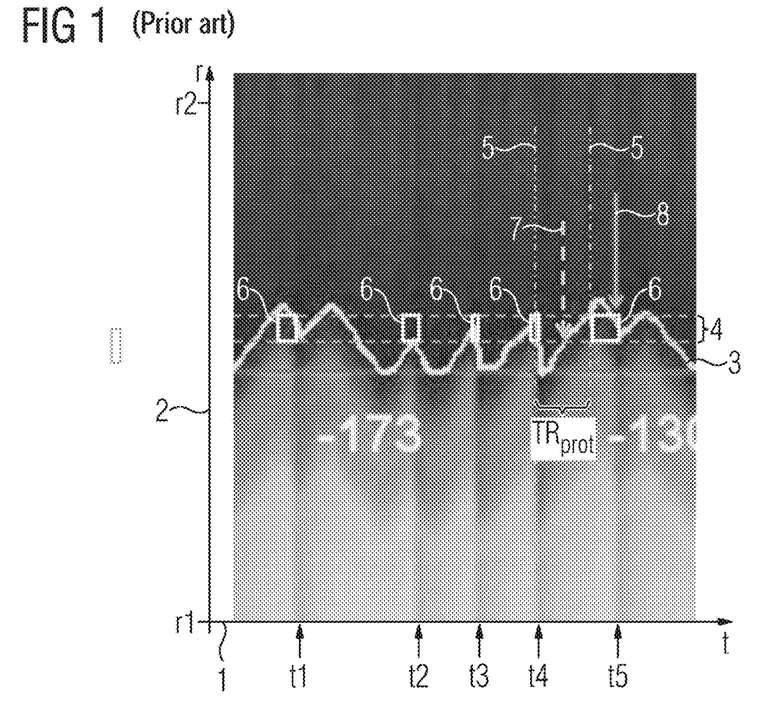
FIG. 1 depicts an exemplary diagrammatic representation to illustrate delayed triggering in the case of a conventional measurement triggered based on breathing.

FIG. 1 illustrates such undesirable influencing of the respiration triggering. For this, the time t is plotted on an x-axis 1 and a location or a location coordinate r is plotted on a y-axis 2. For the present representation a position or relative position of a diaphragm of a patient was detected by an MR navigator sequence. The location r along a longitudinal axis of the body of the patient in the region of the diaphragm is plotted on the y-axis 2 here. Measured values from the liver are plotted in the case of r1 and measured values from the lungs in the case of r2. A position of the diaphragm between the liver and the lungs corresponds with a breathing cycle of the patient and accordingly changes cyclically with time while the patient breathes. Shown superimposed here is a corresponding respiration curve 3, which describes or reflects the relative position determined from MR data measured with the navigator sequence, the cyclical movement of the diaphragm therefore. The respiration curve 3 and the underlying data, measured by the MR navigator sequence, are not continuously acquired and illustrated here, but with jumps in time or interruptions at instants t1, t2, t3, t4, and t5. Here, in each case, a single measurement was triggered for recording MR measurement data from a different region of the patient for a measured data set and therefore the MR navigator sequence for acquiring the respiration curve 3 was interrupted.

Furthermore, in the present case, an acquisition window 4 is specified and illustrated by two broken reference lines, running parallel to the x-axis 1. The acquisition window 4 defines a value range or a value interval in which the respiration curve 3 has to currently be running in each case as a necessary trigger operation. It is therefore a necessary but not solely sufficient condition for a trigger that a last-measured relative position in each case of the diaphragm falls in the acquisition window 4. A further specified, necessary trigger condition that is relevant here is that since the last trigger or trigger event in each case, a time has elapsed which is longer than or equal to the specified reference repetition time $TR_{prot}$. A time interval of length $TR_{prot}$ is illustrated here by way of example by two reference lines 5. Further trigger conditions may also be specified.

Furthermore, a plurality of acceptance windows 6 is identified here. The acceptance windows 6 identify regions for which corresponding checking of all necessary trigger conditions, with the exception of the condition that the last-measured diaphragm position lies inside the acquisition window 4, has resulted, that the respective trigger condition is met. This does not necessarily mean that the excepted condition is not met in the regions of the acceptance windows 6 but only that this condition for displaying the acceptance windows 6 is not being checked or has not been checked. One of the necessary trigger conditions here is that the patient exhales, the respiration curve 3 is in the exhalation phase therefore.

A single measurement for the acquisition of MR measurement data for the data set is therefore triggered when the respiration curve 3 occurs in one of the acceptance windows 6 and this has been automatically identified. An (e.g., specified) optimum trigger instant, a cycle point within the cyclical respiration curve 3 therefore, at which a respective trigger may occur in a particular breathing cycle, is identified here by a first arrow 7, by way of example for a breathing cycle.

In the present representation, a rise in the respiration curve 3 corresponds to an exhalation and a drop in the respiration curve 3 to an inhalation. A trigger may therefore be activated in each case when the respiration curve, increasing from smaller values, during an exhalation therefore, occurs in the acquisition window 4. At the optimum trigger instant identified, (for example, by the first arrow 7), a trigger cannot occur in the present case, however, because the specified reference repetition time $TR_{prot}$ has not yet elapsed since the last trigger at instant t4.

At the identified optimum trigger instant, it had already been detected that the respiration curve 3 is located in an exhalation phase, so the next acceptance window 6 is displayed immediately after expiry of the specified reference repetition time $TR_{prot}$. After expiry of the identified specified reference repetition time $TR_{prot}$, in the present case the respiration curve 3 already lies above the acquisition window 4, however, so initially no triggering occurs. Instead, delayed triggering occurs in the present case at an instant identified by a second arrow 8, at which instant the last-measured position of the diaphragm, the respiration curve 3 therefore, falls in the corresponding acceptance window 6.

For an observer, it is possible to clearly see that at this instant the respiration curve or the breathing cycle is already in a subsequent inhalation phase. No triggering may occur thereby at this instant because, as one necessary operation, it is specified that triggering may only occur during an exhalation phase. A threshold value for identifying a change in the breathing cycle or the breathing phase is specified, however, which takes account of the fact that the signal underlying the respiration curve 3 is noisy and may therefore vary owing not only to breathing but also owing to the noise. The result of this is that at the instant identified by the second arrow 8 it has still not yet automatically been identified that the respiration curve is already in the subsequent inhalation phase. Therefore, in the present case, a delayed trigger or mistrigger occurs at the instant identified by the second arrow 8, and this results in a single measurement for acquisition of MR measurement data for the measured data set being activated at instant t5. Here, the corresponding MR measurement data is therefore not acquired at the optimum instant or during the optimum phase during the breathing cycle or the respiration curve 3. Consequently, an irregular effective repetition time $TR_{eff}$ and a deterioration in image quality ultimately result. No trigger may be generated or activated at the optimum instant or cycle point within the breathing cycle identified by the first arrow 7, however, because acquisition of MR measurement data at this instant may lead to the specified maximum SAR value $SAR_{max}$ being exceeded, and this would in turn lead to immediate stoppage of the measurement.

Experience has shown that an individual adjustment of the specified reference repetition time $TR_{prot}$ to the individual breathing cycle or the individual breathing frequency of the respective patient overtaxes many operators or users. Accordingly, the specified reference repetition time $TR_{prot}$ is conventionally significantly shorter than a breathing cycle of most patients. As described, this disadvantageously leads to unnecessary limiting of parameters of the MR measurement or sequence for most patients and suboptimum or varying triggering, delayed triggering or mistriggering therefore, for a few patients having an unusually short breathing interval in the order of magnitude, of similar length therefore, like/to the specified reference repetition time $TR_{prot}$.

Figure 2:
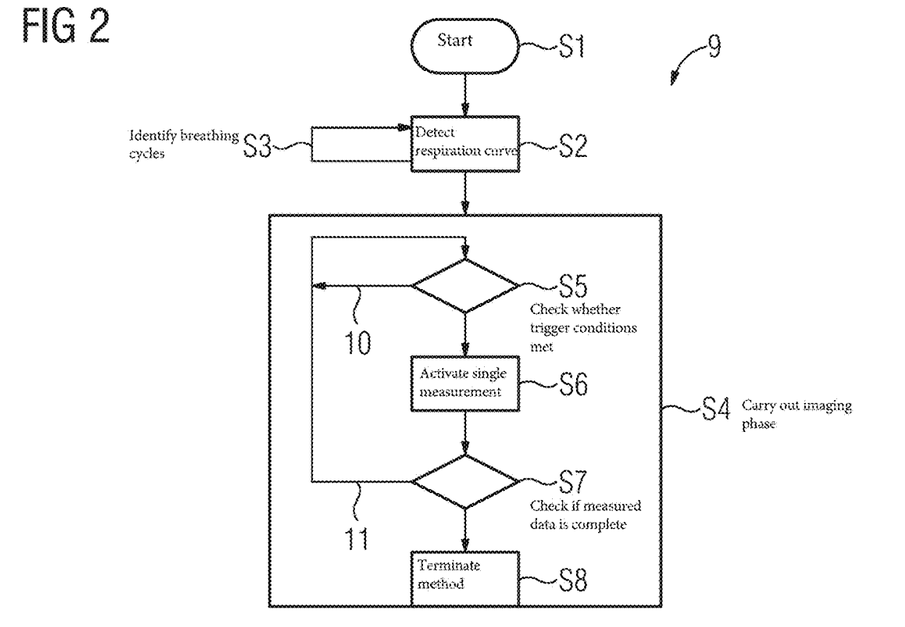
FIG. 2 depicts an exemplary schematic flowchart of a method for triggered acquisition of a measured data set.

To counter these problems, there is therefore a need for an improved method. FIG. 2 depicts an exemplary schematic flowchart 9 for such an improved method for triggered acquisition of a measured data set in a plurality of single measurements, which is robust with respect to situations in which the specified reference repetition time $TR_{prot}$ is at least as long as the mean breathing cycle of the respective patient. The method begins in a method act S1. Here, for example, the patient may be positioned in the respective magnetic resonance system, the magnetic resonance system activated, and a sequence or a protocol specified or adjusted for the MR measurement and corresponding parameters.

Detection of the respiration curve 3 of the patient is started in a method act S2. During what is known as a learning phase, the breathing or the respiration curve 3 is merely detected and analyzed to find, determine, or establish suitable features or properties which are used for defining triggering or trigger events, to generate a trigger in a subsequent measuring or imaging phase therefore, to be able to activate a corresponding single measurement therefore. A trigger is accordingly still not generated during this learning phase. Corresponding triggers are only generated in the imaging phase explained further below if the features or trigger conditions defined during or at the end of the learning phase are met by a value last-measured in each case or signal point of the respiration curve 3. In the present case, the learning phase may include five complete breathing cycles of the patient.

A respective breathing phase is determined, start and end instants of the individual cycles or breathing cycles determined, and corresponding maximum or end values determined and the mean cycle length of the identified cycles calculated as early as during the learning phase for each measured value or signal point of the respiration curve 3, a corresponding underlying cyclical signal therefore.

A start may also already be made on consecutively counting or numbering the identified breathing cycles. The identification of the individual breathing cycles and breathing phases and the consecutive counting or numbering of the breathing cycles is continued during the method, also in the subsequent imaging phase therefore, up to an end of the method, and this is identified here as method act S3 by a loop-shaped path.

Figure 3:
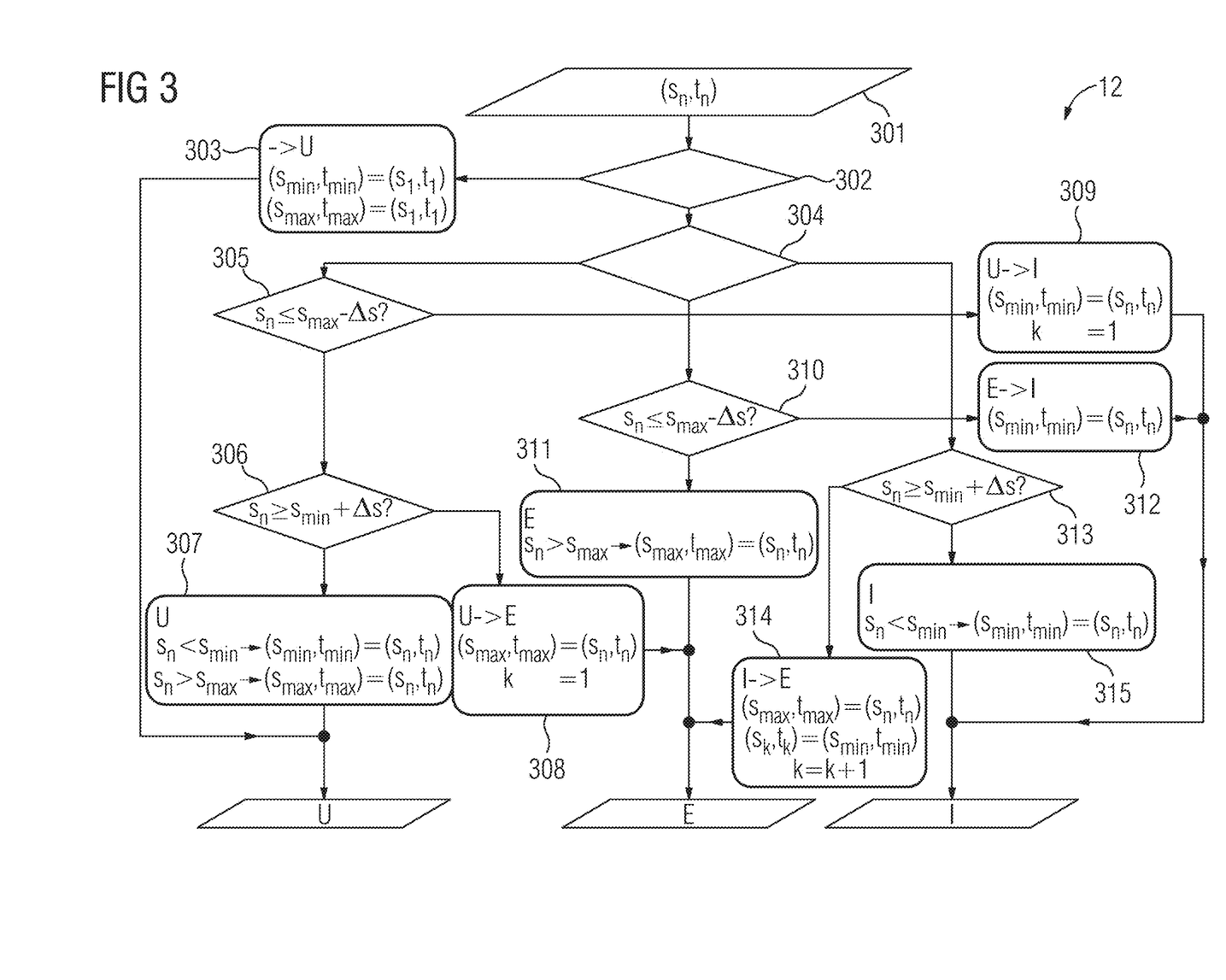
FIG. 3 depicts an exemplary schematic program diagram to illustrate an algorithm for allocation of a respective breathing phase to measured values of a respiration curve.

FIG. 3 depicts an exemplary schematic program diagram 12 to illustrate an algorithm, which may be executed during method act S3 to allocate a respective breathing phase to the measured values of the respiration curve 3 and to determine the current breathing cycle or breathing interval. An end inspiration state, a maximum value or end value at the end of a respective exhalation phase, and therewith at the end of the respective breathing cycle, is allocated moreover to each concluded breathing cycle. The end inspiration state is a tuple including at least one signal value and an associated time stamp at which this signal value was acquired or measured.

In the present case, a sequence of physiological signal points $((s_1,t_1), (s_2,t_2), \ldots, (s_n,t_n))$, of measured values of the respiration curve 3 therefore, is detected. Each signal point of the sequence is a tuple including a measurement or signal value $s_n$ and a time stamp $t_n$. The signal values $s_n$ are noisy. Accordingly, the signal values $s_n$ may therefore each be written as $s_n=q_n+n_n$, where $q_n$ is an unknown actual physiological state, here the actual position of the diaphragm at instant $t_n$ therefore, and $n_n$ is a similarly unknown noise component.

Without limiting the generality, it is assumed here that a local maximum of the sequence $(q_n)$ corresponds to a state at the end of a respective exhalation phase, an end expiration state therefore, and a local minimum of the sequence $(q_n)$ corresponds to a state at an end of a respective inhalation phase, the respective end inspiration state therefore. This assumption serves here merely to simplify the description. If the signal sequence is reversed, all signal values $s_n$ may accordingly be multiplied by −1 and otherwise the described method is applied analogously. Such a reversed signal sequence may be given, for example, if the respiration curve 3 is not detected by the magnetic resonance system with an MR navigator sequence, but as a chest girth of the patient measured by a breathing belt.

The aim of the algorithm is to determine the current breathing phase respectively, at any instant $t_n$ from the previous signal points without knowing the future signal points $(s_{n+1},t_{n+1}), (s_{n+s},t_{n+2}), \ldots$. The breathing phase is a triplet which may assume the states "unknown" (U), "exhalation" (E), "inhalation" (I). The value or state U, E, or I may therefore be allocated to each signal point as a breathing phase. At the beginning of the respective measurement, the breathing phase is unknown. As soon as the state or the breathing phase "unknown" has been left, however, by allocation of the state E or of the state I at a signal point, the state U is no longer attained, is no longer allocated therefore, up to the end of the method.

If the sequence $(q_n)$ were known, the problem would be trivial. Exhalation (expiration) may be inferred from $q_n>q_{n-1}$ and inhalation (e.g., inspiration) may be inferred from $q_n<q_{n-1}$. In the case of $q_n=q_{n-1}$ the respective previous state would be maintained.

A further input for the algorithm is a specified threshold value parameter $\Delta s$, which, clearly expressed, distinguishes a noise from a physiologically substantiated change in the signal sequence. $\Delta s$ may be determined, for example, by a one-time calibration from a standard deviation of the sequence $(s_n)$. If, as in the present example, the respiration curve 3 as the position of the diaphragm is measured by an MR navigator sequence as the cyclical signal, for example, $\Delta s=4$ mm may be used as an empirical value. In the present case, $\Delta s$ may be determined, however, as:

$$\Delta s = \alpha \frac{1}{M-1} \sum_{m=2}^{M} |s_m - s_{m-1}| \quad (7)$$

where $\alpha$ indicates a mean deviation between two successive signal points. Averaging is done in the present case over M signal points measured during the learning phase. M is chosen to be of such a size that averaging is carried out over at least one complete breathing cycle. A value for $\alpha$ may be specified and allows the algorithm to be trimmed. A smaller value of $\alpha$ shortens a delay with which a change in the breathing state, the breathing phase therefore, is registered. By contrast, a larger value of $\alpha$ increases a robustness of the method with respect to noise. Empirically, for example, $\alpha=3$ has proven to be advantageous.

The algorithm may be understood as a state machine (e.g., Finite State Machine or FSM).

In a block 301, the measured physiological signal points $(s_1,t_1), (s_2,t_2), \ldots, (s_n,t_n)$ are successively transmitted or supplied in the sequence in which they were measured as input data or input values to the algorithm or to the finite state machine. In a block 302, it is queried whether the respective input value $(s_n,t_n)$ of the first measured signal point is $((s_n,t_n)=(s_1,t_1))$. If this is the case, in a block 303, the breathing phase U is allocated to this input value, this signal point therefore. A variable k of a breathing cycle counter, which counts off, numbers therefore, the identified breathing cycles is undefined. k may be initialized for example with 0. A sequence of end inspiration states $(s_k,t_k)$ is empty.

If the finite state machine is in this state, a previously measured maximum signal value $s_{max}$ and a previously measured minimum signal value $s_{min}$ are recorded together with the associated time stamps $t_{max}$, $t_{min}$. The following initialization occurs with the measurement and processing of the first signal point $(s_1,t_1)$ therefore: breathing phase="unknown" (U); $(s_{min},t_{min})=(s_1,t_1)$; $(s_{max},t_{max})=(s_1,t_1)$; k=0; sequence of the end inspiration states $(s_k,t_k)$ empty.

Each new measurement, each new signal point $(s_n,t_n)$ therefore, where n>1 (query block 302) may trigger a transition into the state or into the "exhalation" (E) or "inhalation" (I) breathing phase. For this, firstly the instantaneous or current breathing phase, that breathing phase therefore which was allocated to the preceding signal point, is queried in a block 304.

Following processing of the first signal point $(s_1,t_1)$, as described, the current breathing phase is U. In this case, it is then checked in a block 305 for the signal point $s_n$ currently being processed whether the following applies:

$$s_n \leq s_{max} - \Delta s. \tag{8}$$

If this is not the case, it is then checked in a block 306 whether the following applies:

$$s_n \geq s_n + \Delta s. \tag{9}$$

If this is not the case either, the signal value $s_n$ does not affect a state transition, a change in the current breathing phase therefore, and the current breathing phase U is maintained. In addition, the variables $s_{min}$, $t_{min}$ and $s_{max}$, $t_{max}$ are updated in a block 307:

$$s_n < s_{min} \rightarrow (s_{min},t_{min})=(s_n,t_n)$$

$$s_n < s_{max} \rightarrow (s_{max},t_{max})=(s_n,t_n). \tag{10}$$

If, on the other hand, the query or check in block 306 produces a positive result, a transition into the "exhalation" (E) state occurs in a block 308, the breathing phase E is allocated to the signal point currently being processed therefore. The current breathing phase E and the maximum measured signal value in this breathing phase is then updated therefore to $(s_{max},t_{max})=(s_n,t_n)$. $s_{max}$ is here a variable, which records the maximum signal value since the current transition into the state E, where $t_{max}$ is the associated time stamp. The breathing interval counter or breathing cycle counter k is set to 1: k=1.

If the query or check in block 305 produced a positive result, a transition into the "inhalation" (I) state occurs in a block 309 and the minimum measured signal value in this breathing phase is updated to $(s_{min},t_{min})=(s_n,t_n)$. Here, $s_{min}$ is a variable, which records the minimum signal value since the current transition into the "inhalation" (I) state, where $t_{min}$ is the associated time stamp. The current breathing phase and the breathing phase allocated to the signal point currently being processed is then I. The breathing interval counter or breathing cycle counter k is set to 1: k=1.

If, on the other hand, when checking the state of the finite state machine in block 304 it is found that the current breathing phase is "exhalation" (E), with measurement of a new signal point $(s_n,t_n)$ or with processing of the respective current signal point $(s_n,t_n)$ either the state E may be maintained or a transition into the state I may occur. For this, it is checked in a block 310 whether the condition in equation (11) is met:

$$s_n < s_{max} - \Delta s \tag{11}$$

If this is not the case, then the current state, (the current breathing phase E therefore), is maintained and the variables $s_{max}$, $t_{max}$ are updated if the current signal values $s_n$ are greater than the current $s_{max}$, greater than the greatest signal value therefore, which has been measured since the transition into the current state E:

$$s_n > s_{max} \rightarrow (s_{max},t_{max})=(s_n,t_n). \tag{12}$$

If the query or check in block 310 produces a positive result, that the corresponding condition is met therefore, a transition into the "inhalation" state or breathing phase (I) occurs in block 312 and the variables $s_{min}$, $t_{min}$ are initialized with the values of the signal value currently being processed: $(s_{min},t_{min})=(s_n,t_n)$. The current breathing phase, which is allocated to the signal point currently being processed, is then I.

If it is found in block 304 that the current breathing phase is I, with measurement of a new signal point $(s_n,t_n)$ or with processing of the current signal point $(s_n,t_n)$ in each case, the state I may be maintained or a transition into the state E may occur. For this, it is checked in block 313 whether the condition in equation (13) is met:

$$s_n \geq s_{min} + \Delta s \tag{13}$$

If this is not the case, it is maintained as the current breathing phase and the variables $s_{min}$, $t_{min}$ are updated in a block 315, if the current signal value is smaller than the current value $s_{min}$, than the smallest signal value measured during the current breathing phase therefore:

$$s_n < s_{min} \rightarrow (s_{min},t_{min})=(s_n,t_n) \tag{14}$$

If, on the other hand, the query or check in block 313 produces a positive result, the transition into the state or the breathing phase E occurs in a block 314. The variables $s_{max}$, $t_{max}$ are also initialized in block 314 with the values of the current signal point with this transition: $(s_{max},t_{max})=(s_n,t_n)$. The current or then preceding breathing interval is also concluded with this transition. For this reason, the minimum signal value $s_{min}$ recorded during the elapsed "inhalation" breathing phase together with the associated time stamps $t_{min}$ is stored as the end inspiration state of the preceding breathing interval k as a new element of the sequence of the end inspiration states: $(s_k,t_k)=(s_{min},t_{min})$. The variable k, the breathing interval counter therefore, is then incremented by 1: k=k+1.

In this way, a breathing state, (a breathing phase therefore), is allocated to each new signal point $(s_n,t_n)$. This allocation depends implicitly across the instantaneous state respectively of the finite state machine and the variables $s_{min}$, $s_{max}$ on the previously measured signal points but not on the future signal points $(s_{n+1},t_{n+1})$ $(s_{n+2},t_{n+2})$, ..., which are still unknown in the case of the prospective decision at the respective instant. As soon as the initial state "unknown" has been left, a breathing interval or breathing cycle k is also allocated to each signal point $(s_n,t_n)$. An end inspiration state is also allocated to each concluded breathing cycle, the measured values or intervals where 1, 2, ..., k−1 therefore. The entirety of the end inspiration states forms the sequence of the end inspiration states $(s_k,t_k)$. The mean or median length or duration $L_m$ of the identified breathing cycles and their standard deviation $\sigma$ or $\tilde{\sigma}$ may be calculated based on this sequence.

It should be noted at this point that digital filtering or smoothing of the sequence $(s_n)$ may advantageously be omitted.

At the end of the learning phase, the mean or median duration $L_m$ of the breathing cycles, breathing intervals or breathing periods, the period durations of the respiration curve 3 therefore, is determined during the learning phase. The specified reference repetition time $TR_{prot}$ is then compared with the determined mean or medial duration $L_m$. More precisely, the smallest number n≥1 is determined, which satisfies the in equation:

$$(n \cdot L_m - x \cdot \sigma) > TR_{prot} \quad (15)$$

Here, σ is the root of the mean quadratic deviation of the breathing cycles measured during the learning phase from $L_m$ and x is a free parameter, with the aid of which a sensitivity to a detection of a "Short Cycle Modus" may be defined. Values for x may lie in a range between 0.5 and 1.

If the in equation (15) is already met for n=1, there is no change compared to conventional triggered measuring methods and, as a rule, one trigger per breathing cycle is generated or activated. The effective repetition time $TR_{eff}$ of the measurement on successful triggering in each breathing cycle is thereby then equal to the mean duration $L_m$.

If, by contrast, the in equation (15) is met only for n>1, triggering is permitted only in every $n^{th}$ breathing cycle. This means that then at least n−1 breathing cycles respectively are omitted between two triggers or trigger events, during which no triggers are generated—and, more precisely, not even when all remaining necessary trigger conditions are met. If, for example, n=2, then triggers are generated or permitted only in every second breathing cycle, and there is one complete breathing cycle in each case between two triggers or trigger events respectively, during which no trigger is generated or activated. This omission of a breathing cycle means that the time, which has elapsed since the last trigger respectively, if a new trigger is generated or activated, is longer than the specified reference repetition time $TR_{prot}$. Therefore, a trigger is not delayed in a suboptimum breathing phase.

As described, the respiration sensor supplies a sequence of physiological signal points $((s_1,t_1), (s_2,t_2), \ldots, (s_n,t_n))$ including the respective physiological signal value $s_n$ and an associated time stamp $t_n$. The signal value $s_n$ is correlated here, depending on the respiration sensor used, in a respectively defined and known manner with the breathing of the patient and $t_n$ is a time stamp, which indicates the instant of measurement of the signal value $s_n$. As described, in the present case the breathing of the patient, the respiration curve 3 therefore, may be detected with what is known as an MR navigator. A navigator of this type is a short MR sequence, which is inserted in an imaging sequence used for diagnostic imaging of a region of interest (RoI), in order to detect the breathing separately from the RoI.

An excitation pulse of the MR navigator sequence may excite, for example, a two-dimensionally limited rod-shaped region of the patient. In the present case, this region is positioned on a liver dome in such a way that both liver tissue and lung tissue is excited. In a one-dimensional signal read out after this excitation pulse, the position of the diaphragm or a diaphragm edge, which is displaced with breathing, represents a transition between a light or relatively strong signal from the liver and a dark or relatively weak signal from the lungs. The diaphragm edge may then be determined with image processing methods, for example, relative to a specified reference state or reference image. In this example, $s_n$ would be the relative position of the diaphragm edge determined with the last excitation pulse of the MR navigator sequence and $t_n$ would be the instant at which the MR navigator sequence was implemented. Accordingly, $s_{n-1}$ would be the relative diaphragm position last-measured with the MR navigator sequence, or measured previously in each case, at instant $t_{n-1}$, etc.

A breathing interval or breathing cycle may be defined as all signal points, which form part of an expiration phase, exhalation phase therefore, and a subsequent inspiration or inhalation phase. The duration of this breathing cycle may then be defined as the time interval between the states or signal points of maximum inspiration in the current breathing cycle and the state of maximum inspiration, inhalation therefore, in the preceding breathing cycle.

The imaging phase is carried out in a method act S4, the actual measured data set acquired in a plurality of single measurements therefore. It is checked in a method act S5 whether all trigger conditions are met, or a trigger has been generated or activated. This is continuously checked in a loop, and this is indicated here by a path 10. When all trigger conditions are met, a trigger has been generated therefore, a single measurement is activated and carried out in a method act S6 thereby for acquiring MR measured values for the measured data set by the sequence selected in method act S1.

It is then checked in a method act S7 whether the measured data set to be acquired is complete with the preceding single measurement respectively. If this is not the case, the method follows a path 11 to carry out a further single measurement with the next trigger. If the data set has been completely acquired, the method may be terminated in a method act S8.

The described method may be particularly usefully applied, for example, to T2-weighted imaging, for instance, with a turbo-spin echo sequence (TSE), or diffusion-weighted imaging, for instance, with a spin-echo echo-planar imaging sequence (EPI), because here a conventionally desired repetition time is of a similar length to a typical breathing cycle.

Figure 4:
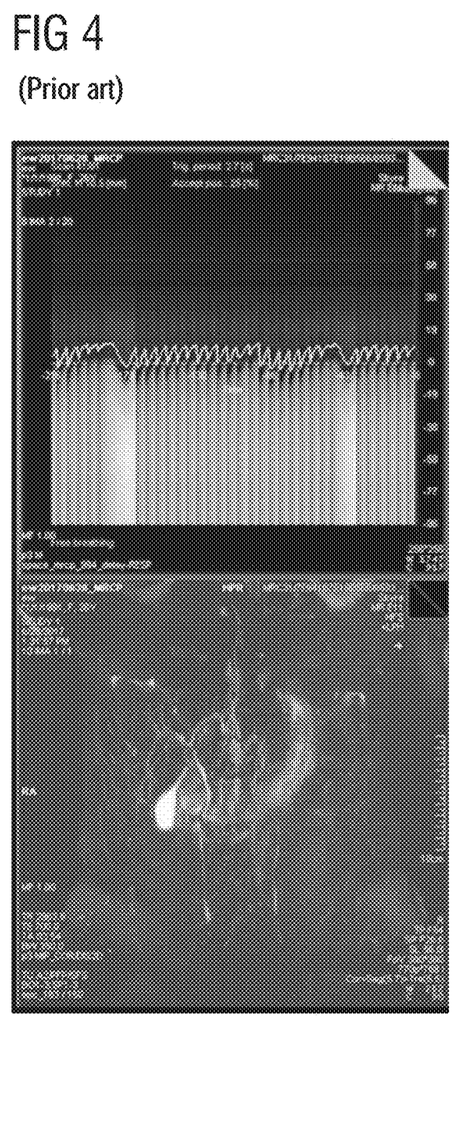
FIG. 4 depicts a representation to illustrate an example of a conventional triggered MR data acquisition and a resulting limited image quality.

FIG. 4 depicts a representation to illustrate a conventional triggered MR data acquisition and a resulting limited image quality owing to an inconsistent or irregular effective repetition time $TR_{eff}$ and, compared to respective optimum trigger instants, delayed mistriggers. An upper part depicts a respiration curve similar to the respiration curve 3 depicted in FIG. 1. A lower part shows a resulting reconstructed MR image. It may clearly be seen in FIG. 4 that triggering is delayed in some breathing cycles by the necessary adherence to the specified reference repetition time $TR_{prot}$ and occurs in a suboptimum breathing phase. Furthermore, there is irregularly no triggering in some breathing cycles, the corresponding breathing cycles are completely omitted therefore, if a different trigger condition is no longer met after expiry of the specified reference repetition time $TR_{prot}$ in each case. This leads to the effective repetition time $TR_{eff}$ for the imaging sequence varying more than the breathing frequency of the patient. Both factors have an adverse effect on the image quality. In the present case, the representation of bile ducts in the lower part is unclear despite regular breathing of the patient. In this example, the specified reference repetition time $TR_{prot}$ is 2,400 ms and the mean length $L_m$ of the breathing cycles 2,700 ms. This applies likewise to the example illustrated in FIG. 5.

Figure 5:
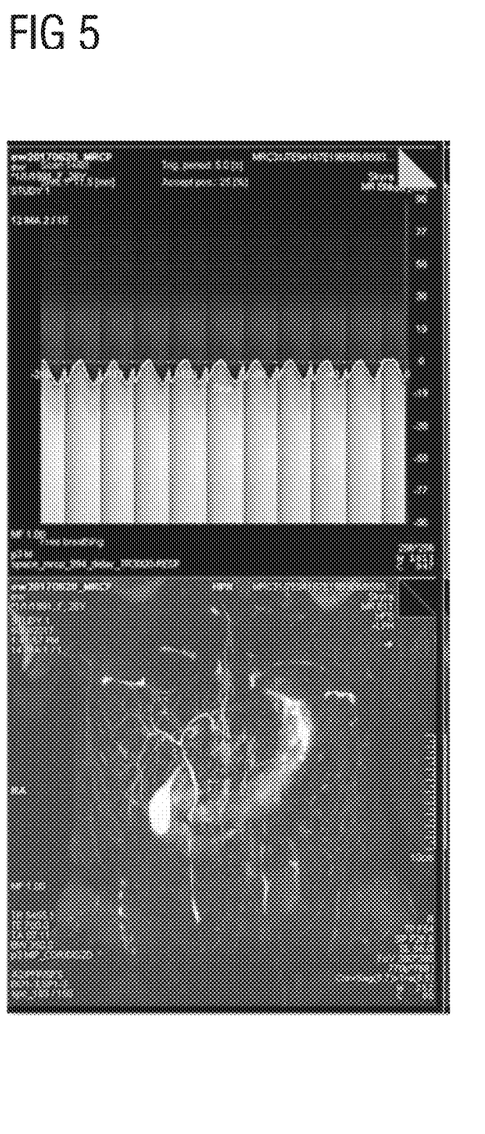
FIG. 5 depicts a representation to illustrate an example of an improved triggered MR data acquisition and a resulting improved image quality.

FIG. 5 depicts a representation to illustrate an MR data acquisition triggered according to the described improved method with temporally uniform triggering at an optimum trigger instant in each case, in the optimum breathing phase in each case therefore, and a resulting improved image quality. Because the specified reference repetition time $TR_{prot}$ here, as in FIG. 4, at 2,400 ms is of a similar length to the approximately 2,700 ms long mean breathing periods, mean duration $L_m$ of the breathing cycles therefore, it has been automatically established in advance here that triggering of a single measurement is permitted only in every second breathing cycle. A complete breathing cycle is omitted therefore in each case between two triggers and accordingly in each case between two single measurements. This provides that triggering is not delayed by adherence to the specified reference repetition time $TR_{prot}$ and the effective repetition time varies over the entire measurement therefore only with the breathing frequency of the patient him-/herself. The bile ducts are shown significantly more clearly and in more detail in the resulting reconstructed image than in FIG. 4.

For the purpose of explanation, it shall now be described here once again what is meant in the present case by respiration triggering or respiration-triggered MR measurement. With respiration triggering, an attempt is made to synchronize an MR measurement with a breathing cycle of a freely breathing patient and to limit the acquisition of MR measurement data, for example, to a relatively quiet breathing phase of the breathing cycle at the end of expiration, at the end of exhalation (e.g., end expiration) therefore. For this, the breathing of the patient is detected as a cyclical, physiological signal. After the initial learning phase of the trigger algorithm, a trigger is generated as soon as a predetermined trigger event has occurred or all necessary specified trigger conditions have been met, for example, a particular breathing phase of the breathing cycle or a particular point within the breathing cycle or within a particular breathing phase is detected or reached. As a result of the trigger, the magnetic resonance system acquires by the specified imaging MR sequence a part, again predetermined, of the data set to be acquired overall from one or more slice(s).

Once this predetermined part, (e.g., a particular data packet), has been acquired, imaging data acquisition automatically stops until the trigger algorithm generates the next trigger. The next part of the data set, (e.g., the next data set), is then acquired by the imaging MR sequence. This sequence is continued until all data has been acquired for the whole data set from all slices.

The trigger conditions may be selected or defined in such a way that triggers are generated during exhalation and in such a way that data acquisition is limited to the relatively quiet phase of the breathing cycle at the end of expiration. A maximum of one trigger per breathing cycle may be generated. A respiration-triggered MR sequence accordingly at most acquires data from a particular slice once per breathing cycle. With sequences in which this data acquisition occurs after one excitation pulse each, the repetition time (TR), the time between two excitations of the same slice therefore, is not fixed, but varies with the breathing cycle, the breathing frequency therefore, of the patient. The repetition time TR is an important parameter in magnetic resonance imaging because a contrast in a resulting image is crucially determined hereby. In respiration-triggered magnetic resonance imaging, reference is made under the conditions to an effective repetition time ($TR_{eff}$), which is equal to the mean length $L_m$ of the breathing cycles of the patient. The length of individual breathing cycles of the patient may be subject to significant individual variations, possibly due to illness, and may be between 3 s and 6 s.

The described examples show how improved image quality may be achieved with particularly straightforward usability for triggered data acquisition.

Although the disclosure has been illustrated and described in detail by the exemplary embodiments, the disclosure is not restricted by the disclosed examples and the person skilled in the art may derive other variations from this without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for triggered acquisition of a measured data set of a target object in a plurality of single measurements by a magnetic resonance system, the method comprising:
   detecting a cyclical signal that describes a cyclical change in at least part of the target object;
   automatically identifying cycles of the cyclical signal;
   automatically determining a mean duration $L_m$ of the identified cycles of the cyclical signal;
   specifying a reference duration $TR_{prot}$ as a reference value;
   determining a smallest whole number n≥1, so an n-multiple of the determined mean duration $L_m$ is longer than the specified reference duration $TR_{prot}$;
   automatically determining whether, in an identified cycle of the cyclical signal, triggering of one measurement of the single measurements is permitted, as a function of the mean duration $L_m$ of the cyclical signal and a specified reference value of an acquisition parameter; and
   permitting the triggering of the single measurements only in each $n^{th}$ cycle of the cyclical signal.

2. The method of claim 1, further comprising:
   defining a cycle point that the cyclical signal has to have reached in a respective cycle as a necessary condition for the triggering of the single measurements.

3. The method of claim 1, further comprising:
   determining an empirical standard deviation σ of durations of the identified cycles of the cyclical signal,
   wherein the number n is determined such that condition $$(n \cdot L_m - x \cdot \sigma) > TR_{prot}$$

is met, where x is a free parameter having a specified value.

4. The method of claim 3, wherein the value of the free parameter x is specified from interval 0.5 to 2.

5. The method of claim 3, wherein the value of the free parameter x is specified from interval 0.5 to 1.

6. The method of claim 1, wherein the identified cycles are consecutively numbered with a consecutive cycle number k,
   wherein one cycle number of the cycle numbers k is allocated to each acquired measured value s of the cyclical signal,
   wherein a maximum value of the cyclical signal is determined for each cycle of the identified, numbered cycles, and
   wherein, from the determined maximum values, a sequence of maximum values is generated.

7. The method of claim 6, wherein the maximum value is an end value of the cyclical signal.

8. The method of claim 1, wherein the single measurements are each shorter than one cycle of the cyclical signal.

9. The method of claim 1, wherein a heartbeat is detected as the cyclical signal.

10. The method of claim 1, wherein a respiration curve is detected as the cyclical signal.

11. The method of claim 10, wherein different phases of the respiration curve are automatically identified,
wherein the different phases comprise an inhalation phase and an exhalation phase, and
wherein the triggering of one measurement of the single measurements is permitted only during the exhalation phase.

12. The method of claim 1, A method for triggered acquisition of a measured data set of a target object in a plurality of single measurements by a magnetic resonance system, the method comprising:
detecting a cyclical signal that describes a cyclical change in at least part of the target object;
automatically identifying cycles of the cyclical signal;
automatically determining at least one property of the cyclical signal comprising determining at which instant $t_n$ in a respective determined cycle an acquired value of the cyclical signal exceeds a specified threshold value or lies in a value interval for a first time; and
automatically determining whether, in an identified cycle of the cyclical signal, triggering of one measurement of the single measurements is permitted, as a function of the at least one determined property of the cyclical signal and a specified reference value of an acquisition parameter,
wherein a maximum SAR value is specified as the reference value for at least one specified time interval, which includes the instant $t_n$, and
wherein the triggering in the respective determined cycle is permitted only when the specified maximum SAR value would not be exceeded by a single measurement triggered at instant $t_n$.

13. A computer program configured to be loaded in a data memory of a magnetic resonance system, wherein when executed by a processor of the magnetic resonance system, the computer program is configured to cause the magnetic resonance system to:
detect a cyclical signal that describes a cyclical change in at least part of a target object;
automatically identify cycles of the cyclical signal;
automatically determine a mean duration $L_m$ of the identified cycles of the cyclical signal;
specify a reference duration $TR_{prot}$ as a reference value;
determine a smallest whole number $n \geq 1$, so an n-multiple of the determined mean duration $L_m$ is longer than the specified reference duration $TR_{prot}$;
automatically determine whether, in an identified cycle of the cyclical signal, triggering of one measurement of a plurality of single measurements is permitted, as a function of the mean duration $L_m$ of the cyclical signal and a specified reference value of an acquisition parameter; and
permit the triggering of the single measurements only in each $n^{th}$ cycle of the cyclical signal.

14. A magnetic resonance system for triggered acquisition of a measured data set of a target object in a plurality of single measurements, the magnetic resonance system comprising:
a detection device configured to detect a cyclical signal, which describes a cyclical change in at least part of the target object;
a measuring device configured to acquire the measured data set; and
a data processing device comprising a data memory and a processor device connected thereto for carrying out program code stored in the data memory, wherein the processor device is configured to:
automatically identify cycles of the cyclical signal;
automatically determine a mean duration $L_m$ of the identified cycles of the cyclical signal;
specify a reference duration $TR_{prot}$ as the reference value;
determine a smallest whole number $n \geq 1$, so an n-multiple of the determined mean duration $L_m$ is longer than the specified reference duration $TR_{prot}$;
automatically determine whether, in an identified cycle of the cyclical signal, triggering of one measurement of the single measurements is permitted, as a function of the mean duration $L_m$ of the cyclical signal and a specified reference value of an acquisition parameter; and
permit the triggering of the single measurements only in each $n^{th}$ cycle of the cyclical signal.

\* \* \* \* \*

UNITED STATES PATENT AND TRADEMARK OFFICE
CERTIFICATE OF CORRECTION

PATENT NO. : 10,989,771 B2  
APPLICATION NO. : 16/515386  
DATED : April 27, 2021  
INVENTOR(S) : Alto Stemmer Page 1 of 1

It is certified that error appears in the above-identified patent and that said Letters Patent is hereby corrected as shown below:

In the Claims

Column 25, Line 10, Claim 12:  
"The method of claim 1, A method for triggered"  
Should be replaced with:  
"A method for triggered"

Signed and Sealed this  
Eighth Day of June, 2021

Drew Hirshfeld  
*Performing the Functions and Duties of the*  
*Under Secretary of Commerce for Intellectual Property and*  
*Director of the United States Patent and Trademark Office*